United States Patent
Tsyb et al.

(12) 
(10) Patent No.: US 6,689,404 B1
(45) Date of Patent: Feb. 10, 2004

(54) AGENT FOR REGULATING IODINE EXCHANGE OR FOR PREVENTING IODINE-DEFICIT CONDITIONS

(75) Inventors: Anatoly Tsyb, Obninsk (RU); Rakhimdzhan Roziev, Obninsk (RU); Valeri Skvortsov, Obninsk (RU); Aleksandr Klepov, Obninsk (RU); Igor Skobelev, Maloyaroslavets (RU); Pavel Us, Obninsk (RU); Victor Kuzin, Obninsk (RU); Anne Goncharova, Obninsk (RU); Leonid Bozadzhiev, Obninsk (RU); Aleksandr Grigoriev, Obninsk (RU)

(73) Assignee: Obschestvo S Ogranichenoi Otvetstvennostou "Medbiofarm", Obninsk (RU)

(*) Notice: Subject to any disclaimer, the term of this patent is extended or adjusted under 35 U.S.C. 154(b) by 0 days.

(21) Appl. No.: 09/763,226
(22) PCT Filed: Aug. 15, 2000
(86) PCT No.: PCT/RU00/00230
§ 371 (c)(1), (2), (4) Date: Apr. 25, 2001
(87) PCT Pub. No.: WO00/78321
PCT Pub. Date: Dec. 28, 2000

(30) Foreign Application Priority Data

Jun. 18, 1999 (RU) .......................................... 99112675

(51) Int. Cl.$^7$ ................................................ A23L 1/304
(52) U.S. Cl. ............................................. 426/74; 426/2
(58) Field of Search ...................................... 426/74, 2

(56) References Cited

PUBLICATIONS

Van Landingham. 1944. The effect of iodated casein (protomone) on milk. J. Dairy Science 27:385–396, abstract only.*

Swolinski, J. 1970. Effect of iodated caseine on milk production of suckling mares. Med.Wet. 26(10) 629–629., abstract only.*

Whitaker, J. and Tannenbaum, S. 1977. Food Proteins, AVI Publishing Co., Inc., Westport, CT. pp. 179–180.*

* cited by examiner

Primary Examiner—Carolyn Paden
(74) Attorney, Agent, or Firm—I. Zborovsky

(57) ABSTRACT

(54) The agent for regulation of iodine exchange or or prophylaxis of iodine deficit. (57) The present invention relates to an agent including iodinated organic compound. The compound includes iodinated proteins and/or its low molecular weight component, such as iodinated polypeptide or the peptide whose structure includes at least one amino acid of the series: phenylalanine, tryptophan.

5 Claims, No Drawings

AGENT FOR REGULATING IODINE EXCHANGE OR FOR PREVENTING IODINE-DEFICIT CONDITIONS

BACKGROUND OF THE INVENTION

The invention concerns to a food-processing industry and can be utilised in medicine and pharmacology, in particular for production of bread, confectionery and pasta, lactic foodstuffs, children's foods, fruit waters and other drinks such as kvass and beer; and also for manufacturing of vitaminized and mineral complexes used for regulation of iodine exchange and for prevent of iodine-deficit.

The problem of iodine deficit is a global problem. The population of many countries have lack of iodine, that leads to diseases of thyroid gland, disturbance of a metabolism which are capable to proceed in oncological disease. Other side of an iodine deficit is low growth and mental dormancy.

There is known applying of salt iodinated alimentary for compensation of lack of iodine coming into an organism. The (NaCl) and inorganic compounds of potassium Iodidum (KI) or potassium iodate ($KIO_3$). 1. Monitoring Universal Salt Iodization Programmes./ Published by PAMM/ICCIDD/MI, 1995. There are following disadvantages in applying of iodinated salt as modern researches have shown. The precise metering. At first it is connected to a high volatility of iodine. During storage and transporting of the product the content of iodine in it is considerably reduced. The nutritions of potassium iodidum are rather unstable to effect of light and dampness. The content of inorganic iodine in iodinated salt during three months is reduced on 50%. The potassium iodate is more stable. However it is unstable too at the presence of impurity of other inorganic salts, at presence of a moisture or temperature drop, at effect gentle acid or alcaline conditions. The instability of these compounds increases at stage of heat treatment of food, for example, during bread baking, which one is characterized by presence both acidic, and alcaline conditions in time of preparation and fermentation of the dough, and also is characterized by effect of high temperatures up to 220° C. in furnace space. Secondly, as researches of world-wide organizations engaging a problem iodine-deficit have shown, the imperfection of present methods of mixing of salt with nutritions of iodine results that the contents of potassium iodidum (iodate) in salt varies from 0 up to 600 parts per one million, Conference on Providing Guarantee of Quality for Programs of Iodizing of Salt, October 1996. In Russia the iodinated salt with the iodine content of 40±15 micro gram per 1 g of the product is applied. At diurnal consumption of salt reaching 10–15 g, 375–825 micro gram of iodine can reach a thyroid gland per day, that in 2.5–5.5 times exceeds its physiological norm. Such high concentrations of iodine in a thyroid gland can call rather undesirable results: disturbance of synthesizing of thyroid Hormonums in a thyroid gland, disturbance of a regulation of a metabolism, development of autoimmune thyroidites and other diseases of a thyroid gland. The data of foreign researches "The incidence of hyperthyroidism in Austria from 1987 to 1995 before and after increase in salt iodization in 1990", obtained on the basis of the analysis of representative sampling, indicate sharp increase of events of diseases of a thyroid gland as a result of applying nutritions of inorganic iodine of a heightened metering. The indicated disadvantage is conditioned by that the organism practically does not participate in regulation of receipt of iodine from inorganic compound into a thyroid gland, because iodine with a blood, passing a liver and gastrointesinal channel, goes into a thyroid gland and can lock up its function when its quantity is heightened. There are also other negative effects of applying of iodinated salt, for example, resulting to impairment of organoleptic properties of food: odor, taste; it is necessary to mark not manufacturability of its obtaining because the precision, expensive equipment for mixing of microquantity of iodine nutritions on macroquantities of salt is required.

The applying of dry starch-iodined complex for treatment of preventative measures of diseases caused by lack of iodine is known also Patent of RU N 2110265, IC AG1 K33/18, published May 10, 1998. Bull. No. 13. Starch-iodined complex, being the organic compound, softer and more natural effects, as the gastrointestinal channel participates in its processing. The applying of the given nutrition increases accuracy of a metering of iodine, going into organism, however it is also poor, because the ratio of distance in starch—carrier of iodine and amylopectin in it are various and depend on sorts, quality, time of collecting and place production of plants, of which starch was manufactured. Quantity of iodine in a known complex is determined by quantity of iodine proceeding at a complex, instead of quantity of iodine, which one can be connected by an amylose, therefore, composition contains iodine in the inorganicm form. Thus, the applying of starch-iodined complex does not allow to execute a precise metering, as well as in case of applying inorganic iodine, and also does not allow personal regulation of iodine exchange, that is conditioned by the process of release of iodine from starch in an organism. There is also such disadvantage that starch-iodine complex can be applied only in a dry form (capsule tablets) and is inapplicable as the alimentary component, as starts to be decomposed already at 40° C.

The foodstuffs including iodine-containing the alimentary components are known, to such products it is possible to attribute bread, milk, oil Guide of Recipes and Technological Instructions for Preparation of Dietetic and Profilactic Sorts of Bread Products. GosNii of Breadbaking Industry, M. Pischeproduct, 1997. Inorganic compounds of iodine, laminaria, yeasty cultures which have been brought up on iodinated water are added into that products as the alimentary components.

Disadvantage of known products is that they have the obviously expressed test and odor, as contain inorganic compounds of iodine, which one have property to be decomposed on light with allocation of free iodine. It is known now that a marine cabbage also contains large reserve of inorganic compounds of iodine. The contents of inorganic iodine and organic iodine in marine cabbage strongly varies depending on a place, conditions, processing and transporting. All known products do not allow to execute personal regulation of iodine exchange of an organism, additionally iodine escapes form them during processing and storage.

The problem facing the authors was finding an agent, which one would allow not only to deliver to an organism missing iodine, but also to execute personal regulation of iodine exchanges. Thus the structure should a long time save stable properties, does not have taste and odor, to be technologic in manufacturing and good in applying.

SUMMARY OF THE INVENTION

The agent of regulation of iodine exchange or preventing iodine deficit including iodinated organic compound is proposed for the solution of a put problem. A distinctive feature of agent is that it contains iodinated proteins and/or its low molecular component, namely the polypeptide or peptide, in a which includes, at least, one of following amino acid: phenylalanine, tryptophan.

DESCRIPTION OF THE PREFERRED EMBODIMENTS

The agent of regulation of iodine exchange or preventing iodine deficit including iodinated organic compound is proposed for the solution of a put problem. A distinctive feature of agent is that it contains iodinated proteins and/or its low molecular component, namely the polypeptide or peptide, in a which includes, at least, one of following amino acid: phenylalanine, tryptophan.

In specific case agent can contain an iodinated casein or iodinated lactoglobulin. Additionally thyrosin and histidin may present in protein structure.

The means may be included into a structure of foodstuff, drink, vitaminized or mineral complex.

The applying of iodinated alimentary protein allows to execute not only compensation of an iodine deficit, but also to execute regulation of iodine exchange, as at consumption of the indicated agent processing of iodine will be following: a gastrointestinal channel-liver-thyroid gland, at which one the organism acquires required dose of iodine, and redundant iodine is injected from an organism, not causing harms. The agent is completely soluted in water, does not lose the properties during several days. In used products there are no offensive organoleptic properties: odor, taste, colouor. A nutrition saves stable properties for a long time. So, for example, the powder of an iodinated casein can be stored in paper packaging, in dry, dark putting, at temperature no more 25 Ñ about 12 months. The iodinated proteins are steady at batch of bread, long save stable properties in a finished product: bread, children's food, confectionery and lactic products. Terms of steady existence of iodinated protein in them is comparable with self lifes of that products and even exceeds them.

The invention is based on the process, for the first time discovered by the authors, of a regulation of iodine exchange of an organism for coming from the outside of iodine-containing protein and/or of their low molecular components. The nutrition works as follows. In a gastrointestinal channel iodinated proteins are decomposed up to iodinated amino acids. The delivery of these amino acids from a gastrointestinal channel into a liver is accompanied by a splitting of iodine from them under effect of an enzyme (deiodinase). The activity of this enzyme is in direct relation to a degree of iodine redundant iodinated amino acids are not the source of iodine for human organism and gradually escape as glucuronides and other compounds. Because of this the overdosage of proposed agent is impossible.

The inventors carried out experimental researches of an iodinated casein, which have confirmed its functional suitability and safety of applying. The mastering of an iodinated casein corresponded to a condition of an organism, being stored more at lack of iodine in a ratio and to a lesser degree at sufficient reception of iodine into an organism. W ere studied both acute, and chronic toxicity of an iodinated casein. In outcome was established, that the excess of the advised single dose in 1000 times and daily dose in 100 times during 30 day does not result in visible changes in organisms of experimental animals. The estimation of allergic properties of iodine-casein was carried out, which one has shown, that iodine-casein does not induce allergic reacting. The similar data are obtained for iodinated lactoglobulin.

The agent is produced as follows. The proteins, for example, milk or hydrolysate of milk protein are soluted in a buffered solution for obtaining their eligible concentration. For iodination can be used either by dry proteins, or hydrolsyate, or natural solution of protein, for example, milk or solution of a hydrolysate of protein. The obtained solution is iodinated with by treatment of iodinated chlorine, or Chloraminum Ó (or Chloraminum Á), or with usage of enzymes in a stoichiometric ratio, or with excess of iodinating agent for full usage of protein, or with lack of the iodinating agent for full usage of iodine. In case of usage of excess of the iodinating agent, solution clean of free iodine through the chemical reducer, for example $Na_2SO_3, Na_2S_2O_3$ etc. iodinated proteins deposit from solution at a decrease of an acidity up to ơ| 3–4. A deposit a protein separate from solution by infiltration or centrifuging. Deposited, washed out and furbished iodinated proteins dry up to damp no more than 5% by lyophilic drying, spray drying or other method.

The agent is applyed as follows. A powder of iodinated protein dilute in water in the ratio 21 g of a powder per 100 ml of water. The obtained solution is added in aqueous phase used for cooking of foodstuff, drink, vitaminized or mineral complex. Different doses of iodine are used for preparation of nutritions for the people of different age groups according to recommendations of WHO. So, for example, for cooking one ton of bread, 5 g of a iodine-casein powder is diluted in 500 ml of water. The obtained solution add in aqueous phase used for preparation of dough. Further process of cooking of bread is continued with known method. Iodine-casein is recommended to apply as the component of drinks including a protein (kwass, beer, lactic productd), etc.). For this dry iodine-casein powder is added directly during cooking a drink at the rate of 5 mg per 1 | of beer or kwass or 2 mg per 1 | of lactic products. In lactic mixes for a children's food such as "Kid" iodine-casein is added at the rate of 6 mg per 1 kg of a mixture. In tablets of calcium gluconate the metering makes 1 mg of iodine-casein on a tablet (at a diurnal consumption 2–3 tablets).

Usage of the invention will allow to decide problems of iodine deficit more effectively.

Sources of Information

1. Monitoring Universal Salt Iodization Programmes. Published by PAMM/ICCIDD/MI, 1995.
2. Conference on Proyiding Guarantee of Quality for Programs of Iodizing of Salt, October 1996.
3. "The incidence of hyperthyroidism in Austria from 1987 to 1995 befor and after increase in salt iodization in 1990", Mostbeck A., Jur J. Nucl. Med. 25, 367–374 (1998).
4. "Target Organ Defects in Thyroid Autoimmune Dizease" Roy S. Sundick, Immunol Rez., 1989; 8; 39–60.
5. Patent of RU N 2 110265, IC A61 K33/18, published May 10, 1998. Bull. No. 13.
6. Guide of Recipes and Technological Instructions for Preparation of Dietetic and Profilactic Sorts of Bread Products. GosNii of Breadbaking Industry, M. Pischeproduct, 1997.
7. Iogine-Enriching Feed Supplement "Amiton", tu, ti, rt 9110-273-05747152-98 (GosNiiKP).

What is claimed is:

1. The agent for regulation of iodine exchange or prophylaxis of iodine deficit including iodinated organic compound distinguished by containing of iodinated protein and/or its low molecular component which includes, at least, one of the following amino acid: phenylalanine or tryptophan, wherein the iodinated protein is iodinated lactoglobulin.

2. The agent according to claim 1, wherein it is a component of foodstuff.

3. The agent according to claim 1, wherein it is a component of vitaminized complex.

4. The agent according to claim 1, wherein it is a component of mineral complex.

5. The agent according to claim 1, wherein it is a component of a drink.

* * * * *